(12) United States Patent
Hu et al.

(10) Patent No.: US 9,388,390 B2
(45) Date of Patent: Jul. 12, 2016

(54) METHOD FOR PREPARING VIRUS-LIKE PARTICLE AND RECOMBINANT BACULOVIRUS USED THEREIN

(71) Applicant: NATIONAL TSING HUA UNIVERSITY, Hsinchu (TW)

(72) Inventors: Yu-Chen Hu, Hsinchu (TW); Shih-Yeh Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 105 days.

(21) Appl. No.: 14/564,512

(22) Filed: Dec. 9, 2014

(65) Prior Publication Data

US 2015/0093804 A1   Apr. 2, 2015

Related U.S. Application Data

(63) Continuation of application No. 13/600,543, filed on Aug. 31, 2012, now abandoned.

(30) Foreign Application Priority Data

Mar. 20, 2012 (TW) .............................. 101109435 A

(51) Int. Cl.
*C12N 7/00* (2006.01)
*A61K 39/00* (2006.01)
*C12N 9/50* (2006.01)

(52) U.S. Cl.
CPC *C12N 7/00* (2013.01); *C12N 9/506* (2013.01); *A61K 39/00* (2013.01); *A61K 2039/5258* (2013.01); *C12N 2710/14143* (2013.01); *C12N 2770/32023* (2013.01); *C12N 2770/32062* (2013.01); *C12N 2770/32351* (2013.01)

(58) Field of Classification Search
None
See application file for complete search history.

(56) References Cited

PUBLICATIONS

Robert R. Granados, Li Guoxun, Anja C.G. Derksen, and Kevin A. McKenna; A New Insect Cell Line from Trichoplusia ni (BTI-Tn-5B1-4) Susceptible to Trichoplusia ni Single Enveloped Nuclear Polyhedrosis Virus; Journal of Invertebrate Pathology, 64, 260-266 (1994).

*Primary Examiner* — Nick Zou
(74) *Attorney, Agent, or Firm* — Rosenberg, Klein & Lee

(57) ABSTRACT

A recombinant baculovirus is provided for preparing picornavirus virus-like particles (VLP), wherein Chitinase A (ChiA) and Cathepsin V (v-cath) genes of the recombinant baculovirus are functionally disrupted and the recombinant baculovirus includes a picornavirus capsid protein gene under control of a strong promoter, and includes a protease gene configured for encoding a protease for hydrolyzing the capsid protein under control of a weak promoter. The recombinant baculovirus of the present invention may adopt High Five or Sf-9 cells for manufacturing enterovirus virus-like particles with improved stability and higher yields in comparison with the conventional arts. A method for preparing virus like particles is also herein provided.

9 Claims, 5 Drawing Sheets

METHOD FOR PREPARING VIRUS-LIKE PARTICLE AND RECOMBINANT BACULOVIRUS USED THEREIN

REFERENCE TO RELATED APPLICATION

This application is being filed as a Continuation Application of patent application Ser. No. 13/600,543, filed 31 Aug. 2012, currently pending.

BACKGROUND OF THE INVENTION

1. Field of the Invention

The present invention relates to a method for preparing picornavirus virus-like particles (VLP) and recombinant baculoviruses used therein, and more particularly to a method for preparing enterovirus virus-like particles and recombinant baculoviruses used therein.

2. Description of the Prior Art

Enteroviruses belong to the Picornaviridae family and are positive-single stranded RNA viruses. Infection often happens via respiratory droplet or stool of an infected person, which can infect multiple systems and organs of a human body and even can cause organ failure. By serum neutralization test, enteroviruses can be classified into Poliovirus (PV), Coxsackie A virus (CAV), Coxsackie B virus (CBV), Enteric Cytopathogenic Human Orphan virus (i.e. Echoviruses), enteroviruses 68-71 and so on.

Being one of the more than 100 enteroviruses serotypes, enterovirus 71 (EV71) is the major etiological agent responsible for hand-foot-and-mouth disease (HFMD) in young children and infants. Children under 5 years of age are particularly susceptible to severe forms of EV71-associated neurological complications such as aseptic meningitis, brain stem encephalitis and even death. Since the 1998 outbreak in Taiwan that caused 405 severe cases and 78 deaths (Ho et al., 1999), in recent years the Asia-Pacific region (e.g. Taiwan, China, Malaysia, Japan and Vietnam) has experienced more frequent EV71-associated HFMD epidemics with high incidence of neurotropic complications and fatality rates (Tee et al., 2010). In 2008, the HFMD outbreak in Taiwan resulted in 373 severe cases and 14 deaths, all due to EV71 infection. The 2008 outbreak in China also led to 489097 reported cases that included 1125 severe cases, and claimed 126 lives. The increasing frequency of EV71 epidemics and high fatality rates underscore the urgent need to develop the vaccines.

VP1 is the major antigen and is highly variable among enteroviruses. Based on the sequences of VP1 gene, EV71 is divided into genogroups A, B and C and subgenogroups within genogroups B and C (B1-B5 and C1-C5).

Traditional viral vaccines include inactivated vaccines and attenuated vaccines, both containing the viral genetic materials and hence posing potential risks. Virus-like particles (VLPs) are empty particles consisting of viral structural proteins but devoid of viral nucleic acids, hence they are non-infectious. VLPs can generally induce broad and strong immune responses thanks to the preservation of many essential epitopes. Therefore VLPs have captured increasing attention as potential vaccine candidates.

Briefly, for the purpose of preventing enteroviruses infection, VLP is a promising vaccine candidate. Enterovirus possesses a positive single-stranded RNA genome that consists of a single open reading frame (ORF). The ORF expresses a large polyprotein that can be cleaved into P1, P2 and P3 regions (Brown and Pallansch, 1995). P1 region encodes the four structural proteins VP1, VP2, VP3 and VP4, while P2 and P3 regions encode other nonstructural proteins (e.g. 2A and 3CD) responsible for virus replication and virulence (Mc-Minn, 2002). Based on a model derived from poliovirus, protease 2A autocatalytically cleaves P1 at its N-terminus and liberates P1 from the nascent polyprotein (Toyoda et al., 1986), while protease 3CD cleaves P1 precursor into VP1, VP3 and VP0 in trans. These three structural proteins spontaneously assemble into icosahedral procapsid in an ordered manner and proceeds through a series of intermediates, followed by the encapsidation of the RNA genome into the provirion. The final encapsidation step involves the cleavage of VP0 into VP2 and VP4, therefore the final mature virion consists of 60 copies each of VP1 and VP3, 58-59 copies of VP2 and VP4 and 2-1 copies of VP0.

Based on the knowledge, the baculovirus expression system has been previously used to co-express the P1 and 3CD proteins of EV71 in insect cells (Hu et al., 2003) and the formation of EV71 VLP in the infected insect cells was demonstrated. The recombinant baculovirus, Bac-P1-3CD, harboring the P1 gene under the polyhedrin promoter and the 3CD gene under the p10 promoter, is constructed using the traditional Bac-to-Bac system. Immunization of mice with the EV71 VLP triggered potent humoral and cellular immune responses and protected mice against lethal virus infection (Chung et al., 2008). However, the VLP yield was too low ($\approx$10-20 μg/ml), making less attractive for commercial production.

SUMMARY OF THE INVENTION

The present invention is directed to a method for preparing picornavirus virus-like particles and recombinant baculoviruses used therein to improve the stability and yield of virus-like particles.

According to an embodiment of the present invention, a recombinant baculovirus comprises a first nucleotide sequence, a first promoter, a second nucleotide sequence and a second promoter. The first nucleotide sequence is used for being translated to a capsid protein of a picornavirus. The first promoter is located in the upstream region of the first nucleotide sequence and comprises p10 promoter, polyhedrin (polh) promoter, p6.9 promoter or capsid protein promoter. The second nucleotide sequence is used for being translated to a protease of the picornavirus, wherein the protease is used to hydrolyze the capsid protein. The second promoter is located in the upstream region of the second nucleotide sequence and is weaker than the first promoter when in the context of baculovirus/insect cell system, wherein Chitinase A (ChiA) and Cathepsin V (v-cath) genes of the recombinant baculovirus are functionally disrupted.

According to an embodiment of the present invention, a method for preparing picornavirus virus-like particles comprises infecting insect cells with the above-mentioned recombinant baculovirus whereby the capsid protein is translated and hydrolyzed by the protease to produce picornavirus virus-like particles and collecting the picornavirus virus-like particles at day 5 or day 6 after the insect cells are infected.

The objective, technologies, features and advantages of the present invention will become more apparent from the following descriptions in conjunction with the accompanying drawings, wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1A:
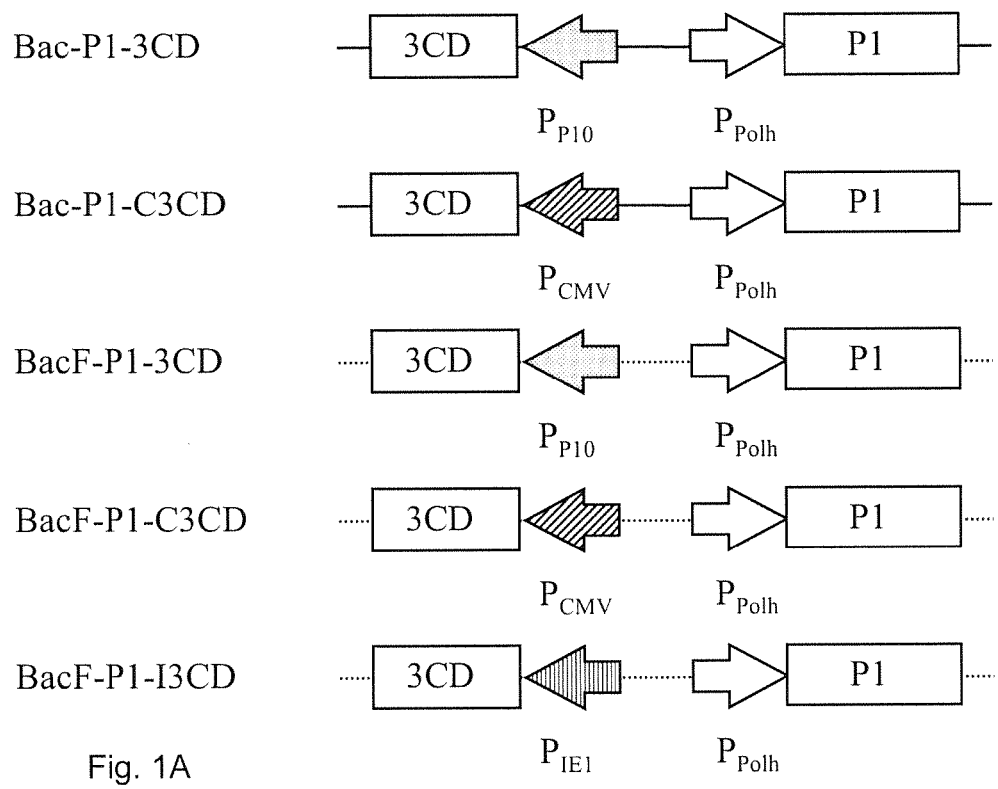
FIG. 1A is a schematic diagram illustrating recombinant baculoviruses according to prior arts and an embodiment of the present invention.

The present invention is directed to a method for preparing picornavirus virus-like particles and recombinant baculoviruses used therein to improve stability and yield of virus-like particles.

According to an embodiment of the present invention, a recombinant baculovirus comprises a first nucleotide sequence, a first promoter, a second nucleotide sequence and a second promoter. The first nucleotide sequence is used for being translated to a capsid protein of a picornavirus. The first promoter is located in the upstream region of the first nucleotide sequence, wherein the first promoter is a strong promoter in the context of baculovirus/insect cell system. The second nucleotide sequence is used for being translated to a protease of the picornavirus, wherein the protease is used to hydrolyze the capsid protein. The second promoter is located in the upstream region of the second nucleotide sequence and is a weak promoter in the context of baculovirus/insect cell system, wherein ChiA and v-cath genes of the recombinant baculovirus are functionally disrupted.

GLOSSARY

Picornavirus: Picornaviruses are RNA viruses and mainly infect human beings and other animals. Picornaviruses comprise human rhinovirus, human poliovirus, human coxsackie virus, human echoviruses, human enterovirus, bovine enterovirus, encephalomyocarditis virus, encephalitis virus, foot-and-mouth disease virus, hepatitis A virus and so on.

Enterovirus: Conventionally, enteroviruses can be classified into Polioviruses (PV), Coxsackie A viruses (CAV), Coxsackie B viruses (CBV). Enteric cytopathogenic human orphan viruses (i.e. Echoviruses, ECHO), enteroviruse 68-71 and so on by serum neutralization test. Recently with the development of DNA sequencing, enteroviruses are alternatively classified into four types A-D and there are more than one hundred of serotypes so far; Enterovirus 71 (EV71) is one type thereof.

An enterovirus genome is approximately 7500 nt in length including an open reading frame (ORF, approx. 6600 nt) and two sides of the enterovirus genome are 5' and 3' untranslated regions (UTR). The ORF can be separated into three regions: P1, P2 and P3 and can be translated to single polyproteins. P1 comprises capsid proteins: VP4, VP2, VP3 and VP1. P2 and P3 comprise non-structural proteins such as protease 2A, 3C and 3CD and polymerase $3D^{pol}$, which contribute to virus duplication and generate virus toxicity.

Strong Promoters and Weak Promoters: People skilled should know appropriate gene expression sequence acting on insect cells (Lo, W.-H., Hu, Y.-C. 2009. Regulation of baculovirus-mediated gene expression. In "Regulation of Viral Gene Expression" (Eli B. Galos, Eds), Nova Science Publishers, Hauppauge. (ISBN: 978-1-60741-224-3)). In some embodiments, the gene expression sequence comprises constitutive promoters. The strong promoters used in insect cells include, but are not limited to, baculovirus p10 promoters, polyhedrin (polh) promoters, p6.9 promoters and capsid protein promoters. The weak promoters used in insect cells include ie1, ie2, ie0, et1, 39K (aka pp31) and gp64 promoters of baculoviruses.

Other non-baculovirus weak promoters in insect cells include, but are not limited to, Bombyx mori cytoplasmic actin gene promoters, Drosophila hsp70 promoters, cytoplasmic actin gene promoters, α-1 tubulin promoters, ubiquitin gene promoters, and cytomegalovirus immediate early (CMV-1E) gene promoters.

Besides, weak promoters can be obtained by attenuating strong promoters, for example, using a truncated segment of strong promoter to attenuate the gene expression ability of strong promoters.

ChiA and v-cath: ChiA and v-cath are two adjacent genes in the Autographa californica multicapsid nuclear polyhedrosis virus (AcMNPV) gene sequence. ChiA protein is an enzyme expressed in the late stage of virus replication, with high activity of extracellular chitinase and intracellular chitinase; v-cath protein is a protease which is in the form of papain and similar to Cathepsin L. ChiA is retained in endoplasmic reticulum (ER) with large quantity after expression with the assistance of an ER positioning sequence KDEL of terminal C of ChiA sequence. ChiA assists the maturation of precursor protein of v-cath (proV-cath), i.e. converting proV-cath into active V-cath to be released after the death of infected cells. Since proV-cath must be folded to become mature enzyme with the assistance of ChiA, it is proved that proV-cath and ChiA have mutual interaction and are accumulated in ER simultaneously. Accumulation of ChiA and proV-cath in ER may block the secretory pathway of secretory proteins.

Additionally, ChiA and proV-cath show chitinase and cysteine protease activity and are released after the death of infected cells. Therefore, these two enzymes are reported to be related to liquefaction of insect bodies after insects are infected with baculovirus and die. The liquefying process of larvae can be mitigated when the baculovirus is defective in ChiA and v-cath genes. Thus, for baculovirus/Bombyx mori expression system, there are many studies using Bombyx mori nucleopolyhedrovirus (BmNPV) recombinant baculovirus, with chiA and v-cath genes removed for generating recombinant proteins, thereby raising the yield of secretory recombinant proteins and decreasing tissue contamination after liquefaction of larvae bodies so as to facilitate follow-up protein purification (Lee et al. Biotechnol Lett 28(9):645-50, 2006; Li et al. Mol Biol Rep 37(8):3721-8, 2010; Li et al. Appl Biochem Biotechnol 165(2):728-36, 2011; Li et al. Mol Biol Rep 38(6):3897-902, 2011). Likewise, on the basis of baculovirus/insect cell expression system, multiple studies have used engineered AcMNPV defective in chiA and v-cath genes to enhance the yield of secretory proteins with mitigated protein degradation (Kaba et al. J Virol Methods 122(1):113-8, 2004; Metz et al. Virol J 8:353, 2011; Possee et al. Biochem Soc Trans 27(6):928-32, 1999). There are also already commercially available recombinant baculovirus vector systems on the market, such as flashBACGOLD (Oxford Expression Technologies Ltd, Oxford. UK) and BacVector-3000 (Novagen, N.J.).

Functional Disruption: There is at least one mutation or structural change in genes to make the genes functionally disrupted, which are substantially unable to generate functional gene products, e.g. chiA or v-cath proteins. In addition, deleting or interrupting necessary transcription unit, polyadenylation signal or splice-site sequence also can generate functional disruption genes. Furthermore, other methods (e.g. antisense nucleotide inhibition of gene expression) can be adopted to achieve functional disruption.

High Five cell: The High Five cell line (BTI-TN-5B1-4, Cat. no. B855-02) was developed by the Boyce Thompson Institute for Plant Research, Ithaca, N.Y. and originated from the ovarian cells of the cabbage looper, *Trichoplusia ni*.

Using flashBACGOLD System to Express Virus-Like Particles

Referring to FIG. 1A, which is a schematic diagram illustrating recombinant baculoviruses according to prior arts and an embodiment of the present invention. Bac-P1-3CD is the baculovirus generated previously based on Bac-to-Bac system (Invitrogen, Carlsbad, Calif.) by Chung et al (Chung et al., 2008; Hu et al., 2003), wherein P1 is driven by polyhedrin promoter while 3CD is driven by p10 promoter and the v-cath and chiA genes are functional. By adopting the commercial flashBACGOLD system, BacF-P1-3CD is generated in which the capsid protein gene P1 of subtype C2 of enterovirus 71 is driven by the polyhedrin promoter and the 3CD protease expression is driven by the p10 promoter. Under the same infection condition (cell density: $2 \times 10^6$ cells/ml, virus dosage: 0.1 MOI), High Five cells are infected by Bac-P1-3CD or BacF-P1-3CD virus and cultured in the shake flask for protein expression. The supernatant is then collected at 2-6 days after infection. Expression and yield of proteins were determined by Western blot analysis and Enzyme-linked immunosorbent assay (ELISA).

Figure 1B:
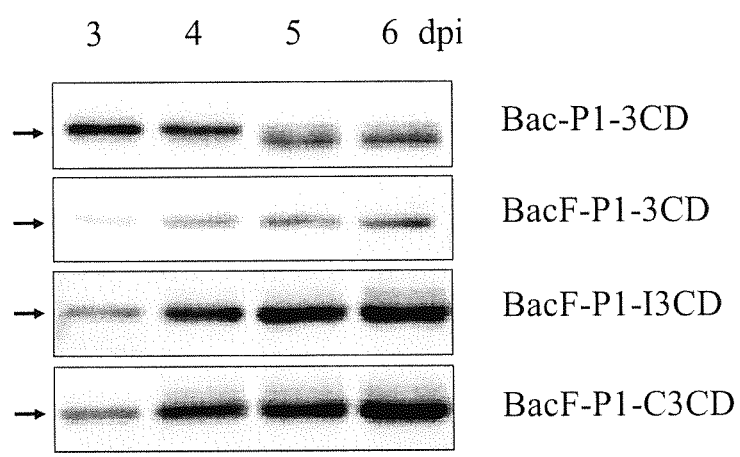
FIG. 1B to 1E is a diagram showing experimental results of the present invention.

Referring to FIG. 1B, according to the Western blot analysis results, BacF-P1-3CD virus constructed using the flashBACGOLD system does not enhance the expression of VP1 (which results from the cleavage of P1 by 3CD and is an indicator of VLP yield), instead the VP1 expression by BacF-P1-3CD is poorer than that by Bac-P1-3CD virus constructed using the Bac-to-Bac® system. The ELISA analyses show that the extracellular VLP concentration conferred by Bac-P1-3CD virus is approximately 18 mg/L and the extracellular VLP concentration conferred by BacF-P1-3CD virus is approximately 5 mg/L. Therefore, the recombinant baculovirus defective in ChiA and v-cath genes constructed using the flashBACGOLD system fails to enhance the EV71 VLP yield when compared with the recombinant baculovirus with functional ChiA and v-cath genes (Bac-P1-3CD). That is, merely using the flashBACGOLD system cannot necessarily enhance the VLP yield conferred by the recombinant baculovirus.

Using Weak Promoters to Drive 3CD Protease Expression

Figure 1C:
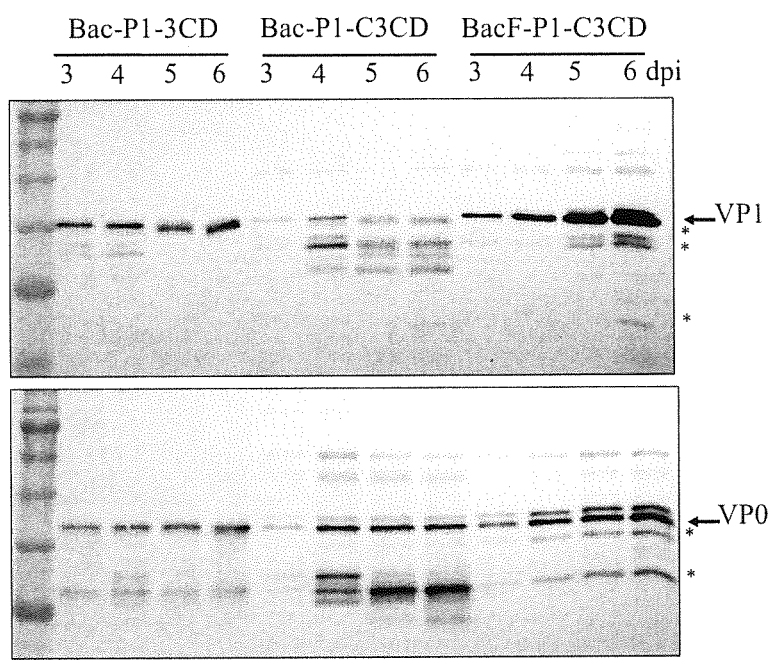

Chung et al. (Chung et al. Vaccine 28(43):6951-7, 2010) constructed recombinant baculovirus vectors Bac-P1-C3CD (FIG. 1A) and Bac-P1-I3CD (not illustrated) using weak promoters such as CMV promoter and baculovirus IE1 promoter to drive the expression of 3CD protease. Such design was based on the hypothesis that reduced 3CD expression can enhance the P1 expression level, because 3CD expression driven by a weak promoter would be less capable of competing with P1 expression driven by a strong promoter for cellular resources and thus boost the EV71 VLP yield (Chung et al. Vaccine 28(43):6951-7, 2010). Indeed, Bac-P1-C3CD (using weak CMV-1E promoter to drive 3CD expression) has achieved higher yield than Bac-P1-3CD (using strong p10 promoter to drive 3CD expression). However, as observed by the inventors, Bac-P1-C3CD infection resulted in abundant degradation products starting from 4 days post-infection as shown in FIG. 1C. The degradation would not be able to enhance the VLP yield and instead cause difficulties for VLP purification. Although we have attempted to increase the yield by means such as modulating the relative expression levels of P1 and 3CD proteins (data not shown), the yield was only moderately increased and the VLP degradation was severe. Therefore, there is still room to improve the VLP yield.

Using IE1 and CMV Promoters to Drive 3CD Protease in the flashBACGOLD System

Referring to FIGS. 1A and 1B, recombinant baculoviruses BacF-P1-I3CD and BacF-P1-C3CD are constructed using the flashBACGOLD system, which use IE1 and CMV promoters to drive 3CD protease, respectively. Under the same condition as above, VLP yield was determined after insect cells were infected with these two strains of recombinant viruses. Western blot analysis (FIG. 1B) illustrates dramatic increase in the VP1 yield starting from day 4 after the cells are infected with BacF-P1-I3CD and BacF-P1-C3CD (when compared with Bac-P1-3CD and BacF-P1-3CD). Referring to FIG. 1C, Bac-P1-C3CD virus causes obvious VP1 protein degradation at 5 and 6 days post-infection (dpi), In contrast, the VP1 produced by BacF-P1-C3CD is more stable with fewer degradation products, thereby significantly elevating the VP1 yield.

Figure 1D:
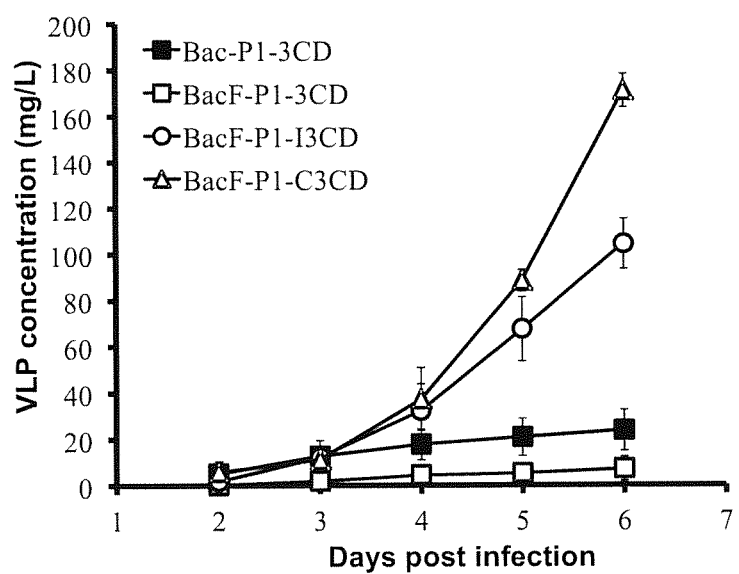

Referring to FIG. 1D, the actual VLP yield in the supernatant is determined by ELISA. At the fourth day, the average VLP yield by Bac-P1-3CD is approximately 18 mg/L and the yield by BacF-P1-3CD viruses is 5 mg/L. At the sixth day, the yield conferred by BacF-P1-I3CD can reach 100 mg/L. Strikingly, the yield conferred by BacF-P1-C3CD amounts to 170 mg/L, which is almost 10 times and 34 times the yield conferred by Bac-P1-3CD and BacF-P1-3CD, respectively.

From the aforementioned data, could be observed from BacF-P1-3CD that merely removing ChiA and v-cath genes from the baculovirus backbone, as in the case of using the flashBACGOLD system, cannot enhance the VLP yield. In the present invention, Bac-P1-C3CD infection was found to generate a large amount of degradation products. The data demonstrate that using the flashBACGOLD system or driving 3CD by a weak promoter along cannot enhance the VLP yield. In contrast, BacF-P1-C3CD, which combines the use of weak promoter to drive 3CD expression and disrupted ChiA/v-cath genes, can solve the degradation problem and achieve increased yield.

Comparison of VLP Yield in High Five and Sf-9 Cells

High Five and Sf-9 are two insect cell lines commonly used for protein production. According to prior research of Chung et al. (Chung et al. Vaccine 28(43):6951-7, 2010), the highest VP1 protein yield (45 mg/L) was achieved by infecting Sf-9 cells with Bac-P1-C3CD, and was obtained on the fourth day after Sf-9 cells were infected with Bac-P1-C3CD. When High Five cells were infected with Bac-P1-C3CD, the highest yield of VP1 protein (~30 mg/L) was obtained on the second day. Therefore, in Chung's system, Bac-P1-C3CD infection in Sf-9 cells would generate higher VP1 protein yield than Bac-P1-C3CD infection in High Five cells.

Figure 1E:
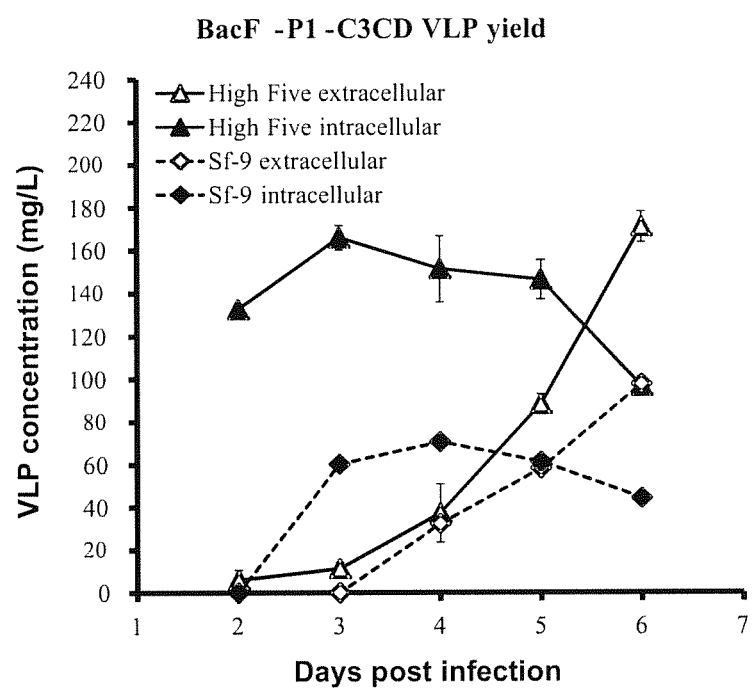

As shown in FIG. 1E, BacF-P1-C3CD infection of Sf-9 cells results in the highest extracellular yield of 100 mg/L at 6 dpi and the highest intracellular VLP yield of 70 mg/L at 4 dpi. In contrast, BacF-P1-C3CD infection of High Five cells results in significantly higher extracellular VLP yield of 170 mg/L (at 6 dpi) and intracellular VLP yield of 160 mg/L at 3 dpi. Therefore, the method for preparing VLP in the present invention is applicable for both High Five and Sf-9 cells and the yields thereof are much higher than those of Chung et al. In addition, High Five can result in significantly higher yield than Sf-9, after infection with the recombinant baculovirus of the present invention, thus High Five is preferable for VLP production in the expression system of the present invention.

In conclusion, the method and recombinant baculovirus used for preparing VLP of the present invention is achieved by using BacF-P1-I3CD and BacF-P1-C3CD recombinant baculovirus to infect High Five cells or Sf-9 cells to generate enterovirus VLP, wherein the VLP generated is more stable with higher yield than both prior arts and methods that merely uses flashBACGOLD, i.e. BacF-P1-3CD.

While the invention is susceptible to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A method for preparing picornavirus virus-like particles, comprising:
   providing a recombinant baculovirus comprising:
   a first nucleotide sequence, for being translated to a capsid protein of a picornavirus;
   a first promoter, located in the upstream region of the first nucleotide sequence and selected from the group consisting of p10 promoter, polyhedrin (polh) promoter, p6.9 promoter and capsid protein promoter;
   a second nucleotide sequence, for being translated to a protease of the picornavirus; and
   a second promoter, located in the upstream region of the second nucleotide sequence, wherein the second promoter is a truncated segment of the first promoter, wherein the second promoter is weaker than the first promoter in the context of recombinant baculovirus infection to an insect cell and ChiA and v-cath genes of the recombinant baculovirus are functionally disrupted; and
   infecting insect cells with the recombinant baculovirus whereby the capsid protein is translated and hydrolyzed by the protease to produce picornavirus virus-like particles; and
   collecting the picornavirus virus-like particles at day 5 or day 6 after the insect cells are infected.

2. The method for preparing picornavirus virus-like particles according to claim 1, wherein the first promoter is selected from the group consisting of polyhedrin promoter and p10 promoter.

3. The method for preparing picornavirus virus-like particles according to claim 1, wherein the insect cell is a Sf-9 cell strain.

4. The method for preparing picornavirus virus-like particles according to claim 1, wherein the insect cell is a High Five cell strain.

5. The method for preparing picornavirus virus-like particles according to claim 1, wherein the picornavirus comprises an enterovirus.

6. The method for preparing picornavirus virus-like particles according to claim 5, wherein the enterovirus comprises enteroviruses 68-71, Coxsackie A viruses or Coxsackie B viruses.

7. The method for preparing picornavirus virus-like particles according to claim 1, wherein the picornavirus virus-like particles are used for preparing a vaccine.

8. The method for preparing picornavirus virus-like particles according to claim 1, wherein the picornavirus virus-like particles are collected at day 5 after the insect cells are infected.

9. The method for preparing picornavirus virus-like particles according to claim 1, wherein the picornavirus virus-like particles are collected at day 6 after the insect cells are infected.

* * * * *